US006853926B2

United States Patent
Alfano et al.

(10) Patent No.: US 6,853,926 B2
(45) Date of Patent: Feb. 8, 2005

(54) SYSTEMS AND METHODS FOR NON-DESTRUCTIVELY DETECTING MATERIAL ABNORMALITIES BENEATH A COATED SURFACE

(75) Inventors: Robert R. Alfano, Bronx, NY (US); Iosif Zeylikovich, Brooklyn, NY (US); Wubao Wang, Flushing, NY (US); Jamal Ali, Brooklyn, NY (US); Vincent Benischek, Shrub Oak, NY (US); Yury Budansky, Oakland, NJ (US)

(73) Assignees: Research Foundation of CUNY, New York, NY (US); Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/455,662

(22) Filed: Jun. 5, 2003

(65) Prior Publication Data

US 2003/0229458 A1 Dec. 11, 2003

Related U.S. Application Data

(60) Provisional application No. 60/385,854, filed on Jun. 5, 2002.

(51) Int. Cl.⁷ ................................................ G01B 5/28

(52) U.S. Cl. .................... 702/40; 702/155; 702/159; 250/399.1; 250/341.8

(58) Field of Search .......................... 702/155, 34, 35, 702/40, 49, 75, 153, 159, 166, 170–172; 250/330, 339.1, 341.8

(56) References Cited

U.S. PATENT DOCUMENTS

| 4,076,984 A | * | 2/1978 | Gromov et al. ............. 250/367 |
| 5,850,466 A | * | 12/1998 | Schott ........................ 382/141 |
| 6,495,833 B1 | * | 12/2002 | Alfano et al. ............ 250/341.8 |
| 2004/0026622 A1 | | 2/2004 | DiMarzio et al. | |

* cited by examiner

*Primary Examiner*—Bryan Bui
(74) *Attorney, Agent, or Firm*—Dilworth & Barrese, LLP (57) ABSTRACT

The present invention provides systems and methods for non-destructively detecting material abnormalities beneath a coated surface, comprising a mid-infrared (MIR) detection unit for illuminating an area of the coated surface and detecting light reflected from the illuminated area of the coated surface, and a processing unit for producing an image from optical characteristics received from the MIR detection unit. In addition, the system may further comprise a scanning unit for moving the MIR detection unit to a next area.

27 Claims, 10 Drawing Sheets

SYSTEMS AND METHODS FOR NON-DESTRUCTIVELY DETECTING MATERIAL ABNORMALITIES BENEATH A COATED SURFACE

PRIORITY

This application claims priority under 35 U.S.C. §119 to a provisional application entitled "System and Method for Corrosion and Cracks Detection Beneath a Paint Layer" filed in the United States Patent and Trademark Office on Jun. 5, 2002 and assigned Serial No. 60/385,854, the contents of which are hereby incorporated by reference.

GOVERNMENTAL INFORMATION

This invention is supported in part by: Air Force Office of Scientific Research (AFOSR) under a grant of #F49620-00-1-0378 (RF 47435-00-01); National Science Foundation (NSF) under a grant of #CMS-0135790 (RF 40357-00-01); and NYS TTIP (Technology Transfer Incentive Program) under a grant of #C2000056 (RF 55414-00-01).

BACKGROUND OF THE INVENTION

1. Field of the Invention

The present invention relates generally to systems and methods for non-destructively detecting material abnormalities beneath a surface, and in particular, to systems and methods for detecting corrosion and cracks in metal surfaces beneath a layer of paint using mid-infrared light.

2. Description of the Related Art

Paint or other coatings are typically applied to surfaces to protect the surfaces against corrosion or other damage. In some instances, corrosion, cracking, or other damage (material abnormality) begins under the paint or coating and is undetectable by visual inspection. In addition, the paint itself may crack, while the underlying surface is perfectly fine. This may cause unnecessary repairs. Conventionally, inspections may be carried out by one or more of the following non-destructive imaging (NDI) techniques.

Ultrasonic (pulse echo or through transmission) methods can monitor larger defects of, for example, aircraft structures for a whole-field, but are not preferred for detection of early or surface deterioration. The techniques are particularly conducive to rapid imaging of a surface and include magneto-optic eddy current imaging, active thermography, optically aided visual inspection, and spectral imaging.

Magneto-optic imaging (MOI) can image corrosion and cracks over a small area the size of the magneto-optic crystal plate used in a hand-held scanner. However, MOI's sensitivity to top-surface corrosion depends on the degree to which the eddy currents are altered and gives rise to anomalies in the induced magnetic field at the surface. It has not been shown conclusively that the MOI technique can detect incipient corrosion that has not yet produced a significant increase in macroscopic surface roughness.

Active Thermography (AT) is an increasingly important technique for detecting subsurface flaws such as delamination, debonding, and second-surface corrosion. AT has a lower sensitivity to incipient corrosion under paint, however, because (1) the initial stages of corrosion do not significantly increase the thermal impedance of the surface compared to a layer of paint alone, and (2) the detailed resolution of incipient corrosion effects at the top surface requires a very high speed infrared camera to resolve surface transients which may appear only in the few milliseconds after the initial flash lamp illumination. In addition, such equipment is prohibitively expensive for use on a wide scale. However, for significant surface corrosion, AT and MOI have the potential to image significant surface corrosion damage and distinguish it from subsurface effects by employing commercially available instrumentation.

Visual Inspection (VI) is used to determine the extent of corrosion damage on a skin of a surface and around fasteners, for example, after the paint or coating has been stripped. As a nondestructive technique for painted aircraft, visual techniques are not amenable to detection of chemical changes or micro-roughness at the paint/metal interface, unless significant corrosion products penetrate through the thickness of the paint.

Spectral Imaging (SI) techniques generally use a compact multi-spectral imaging sensor. This method is based on the partial transparency of many aircraft paints to specific bands of infrared radiation. Using this method, it is possible to detect changes in the chemistry of the metal surface or the primer by analyzing the amplitude of reflected and emitted radiation at specific wavelengths. The layered depth information, i.e., the state of the surface at different depths below the paint, cannot be deduced from a simple SI approach, however.

Photonic techniques offer a potentially rapid, noninvasive and easy approach to detect corrosion in situ. Art preservationists use Near-IR (NIR) charge-coupled device (CCD) cameras ($\lambda < 2\ \mu m$) to view paintings that have underdrawings not visible with the human eye. Novel methods of a second-harmonic generation (SHG) imaging, and spectral polarization optical imaging have been proposed to detect the early stages of corrosion under thin layers of paint using NIR. One such Example of this technique can be found in U.S. Pat. No. 6,495,833, entitled "Sub-surface Imaging Under Paints and Coatings Using Early Light Spectroscopy," which issued to Alfano et al. on Dec. 17, 2002 (hereinafter referred to as "Alfano").

Alfano discloses near-infrared (NIR) optical imaging systems and methods to non-destructively image (NDI) deteriorations or defects in painted metals and artwork beneath painted surfaces. Specfically, back-scattered light is used to determine suitability to monitor corrosion and cracking in metal beneath paints, up to a thickness of about 500 $\mu$m. That is, NIR light, which is in the paint transmission zone spanning from 800 nm to 10,000 nm, can be used to assess the quality of metallic structures below the paint level for incipient and advanced stages of corrosion and cracking. NIR light scattered from paint, corrosion, air voids, and metal can be spatially imaged in micrometer sliced subsurface layers. In addition, spectral, temporal, spatial, nonlinear optical, and polarization gates are employed to distinguish phantoms in turbid media, such as painted corroded metal and cracked specimens, e.g., painted surfaces from airplanes, submarines, ships, automobiles, bridges, etc.

However, the systems and methods disclosed in Alfano, which utilize NIR optical imaging, also require a gating system in order to create the detected images. This gating system and tends to create a more complex and costly imaging system. In addition, at this time, there is no method for detecting the early stages of corrosion under surface thick paint with thickness larger than 40 μm.

Therefore, a need exists for an improved system and method for inspecting surfaces through a coating, such as paint. A further need exists for such a system and method, which improves upon existing techniques and does not suffer from the disadvantages as described above.

SUMMARY OF THE INVENTION

It is, therefore, an object of the present invention to provide improved system and method for detecting corrosion and cracks in metal surfaces beneath a layer of paint.

It is another object of the present invention to provide improved system and method for detecting corrosion and cracks in metal surfaces beneath a layer of paint using mid-infrared light.

It is yet another object of the present invention to provide a system and method for detecting corrosion and cracks in metal surfaces beneath a layer of paint with thickness larger than 40 μm.

To achieve the above and other objects, the present invention provides a system for non-destructively detecting material abnormalities beneath a coated surface, comprising a mid-infrared (MIR) detection unit for illuminating an area of the coated surface and detecting light reflected from the illuminated area of the coated surface, and a processing unit for producing an image from optical characteristics received from the MIR detection unit. In addition, the system may further comprise a scanning unit for moving the MIR detection unit to a next area.

To achieve the above and other objects, the present invention also provides a method for nondestructively detecting material abnormalities beneath a coated surface, comprising the steps of: illuminating an area of the coated surface with an MIR light source; detecting light reflected from the illuminated area of the coated surface; measuring optical characteristics of the reflected light; and producing a 2-D image from information received from a MIR detection unit. Additionally, the method may further comprise scanning a next area.

BRIEF DESCRIPTION OF THE DRAWINGS

The above and other objects, features, and advantages of the present invention will become more apparent from the following detailed description when taken in conjunction with the accompanying drawings in which.

DETAILED DESCRIPTION OF PREFERRED EMBODIMENTS

Several preferred embodiments of the present invention will now be described in detail herein below with reference to the annexed drawings. In the drawings, the same or similar elements are denoted by the same reference numerals even though they are depicted in different drawings. In the following description, a detailed description of known functions and configurations incorporated herein has been omitted for conciseness.

In order to determine an improved method for imaging a below a coated surface, various test were performed in order to determine optimal conditions and specification for the system and method. More specifically, tests were performed to determine an optimal IR-range for performing the subsurface imaging.

Figure 1:
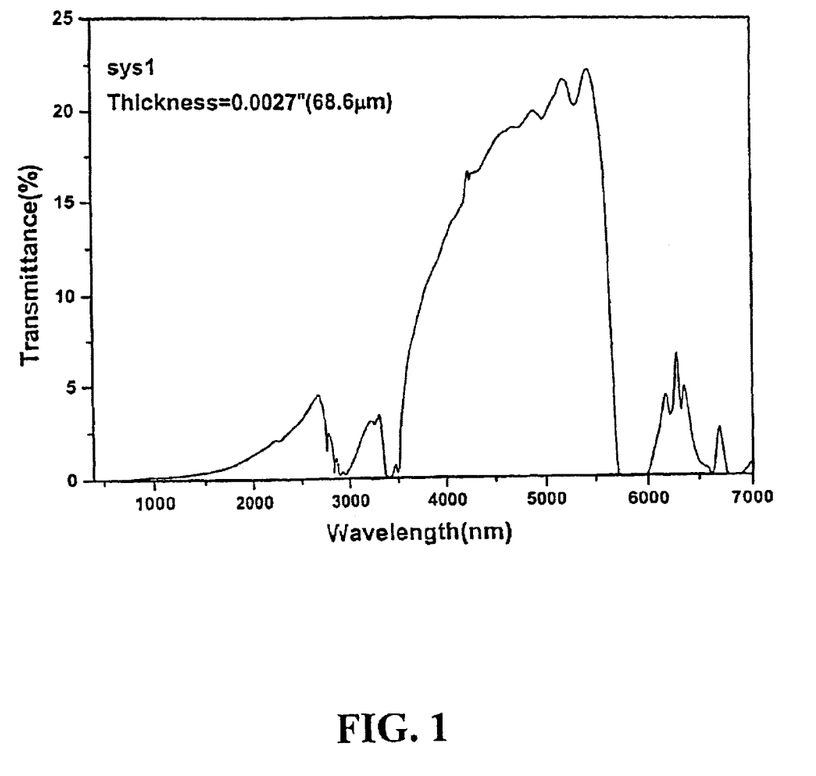
FIG. 1 is a graph illustrating a transmission curve of a paint.

FIG. 1 is a graph illustrating a transmission curve of a paint, in which a transmission zone, e.g., 1 to 7 μm, was measured to define key transmission "windows" for transmission imaging. Significantly progressive results were achieved to obtain data necessary to design the experiments for detecting corrosion and cracks in metal surfaces beneath a layer of paint using mid-infrared light.

In the experiment, the samples used were made from grade 2024 T3 aluminum plates, which were chemically corroded by the reaction of potassium hydroxide with the surface of the aluminum plate for a period of 24 hours. The thickness of the corrosion was about 35 μm and formed an 8 mm circle. The corrosion was either over coated with paint or covered with glass slides that had been prepared with different paints of various thickness. The over coated glass slides were prepared to measure absorption/transmission characteristics of the individual paints. Different commercial and military paints were studied.

The transmission curve of the paint illustrated in FIG. 1 indicates that paint has two transmittance zones for the wavelengths from 1 μm to 2.8 μm and from 3.8 μm to 5.5 μm. Military paint is comprised of a polyurethane primer layer, Strontium Chromate-TT-P-2760 Type 1 Class C, and a polyurethane topcoat, Mil-PRF-85285 Type 1 color 36173 gray. Absorption and scattering are the dominant mechanisms for the results displayed in FIG. 1. When an incident power on the sample at a particular wavelength is large enough, i.e., has a high enough signal to noise (S/N) ratio), imaging through an absorption layer is possible. The problem of imaging through paint layer is more complicated because of high scattering.

Figure 10:
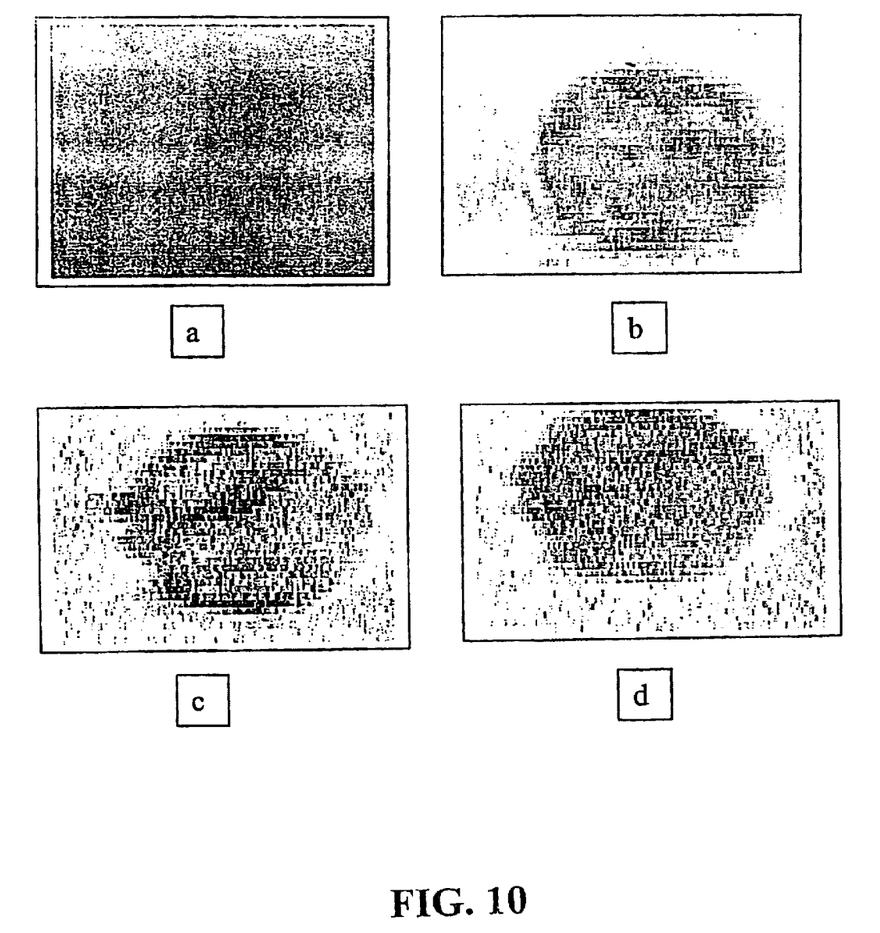
FIG. 10 illustrates images of corrosion on an aluminum plate using an MIR technique.

FIG. 10 illustrates images recorded at different MIR wavelengths. Specifically, FIG. 10 illustrates images at 1.8 μm, 3.8 μm, and 5.5 μm wavelengths, of corrosion over coated with a paint (0.004" thick). Image (a)—is for the 1.8 μm wavelength (an NIR wavelength). Consequently, the corrosion region could not be imaged using NIR, because at this wavelength the transmission of the light is minimum and scattering is maximum compared to the other wavelengths. As the wavelength increases from 1.8 μm wavelength to the 3.8 μm wavelength (Image (b)) the transmission of light through the paint is higher and more photons reach the corrosion surface. The image for MIR of Image (c) (—at 4.8 μm wavelength) has the best contrast, which correlates with the transmission curve of the paint. The optical transmission at 5.5 μm wavelength is less then at 4.8 μm wavelength. Accordingly, this results in the slightly poorer image as illustrated in Image (d).

The present invention provides a novel and useful optical system for scanning and detecting material abnormalities, e.g., cracks and corrosion, beneath a paint layer of an object such as an aircraft, a boat, a car, a bridge, etc. using a NIR and mid-infrared (MIR) light source with a wavelength range from 0.7 μm to 5.5 μm, as illustrated in FIGS. 1 and 10.

Figure 2:
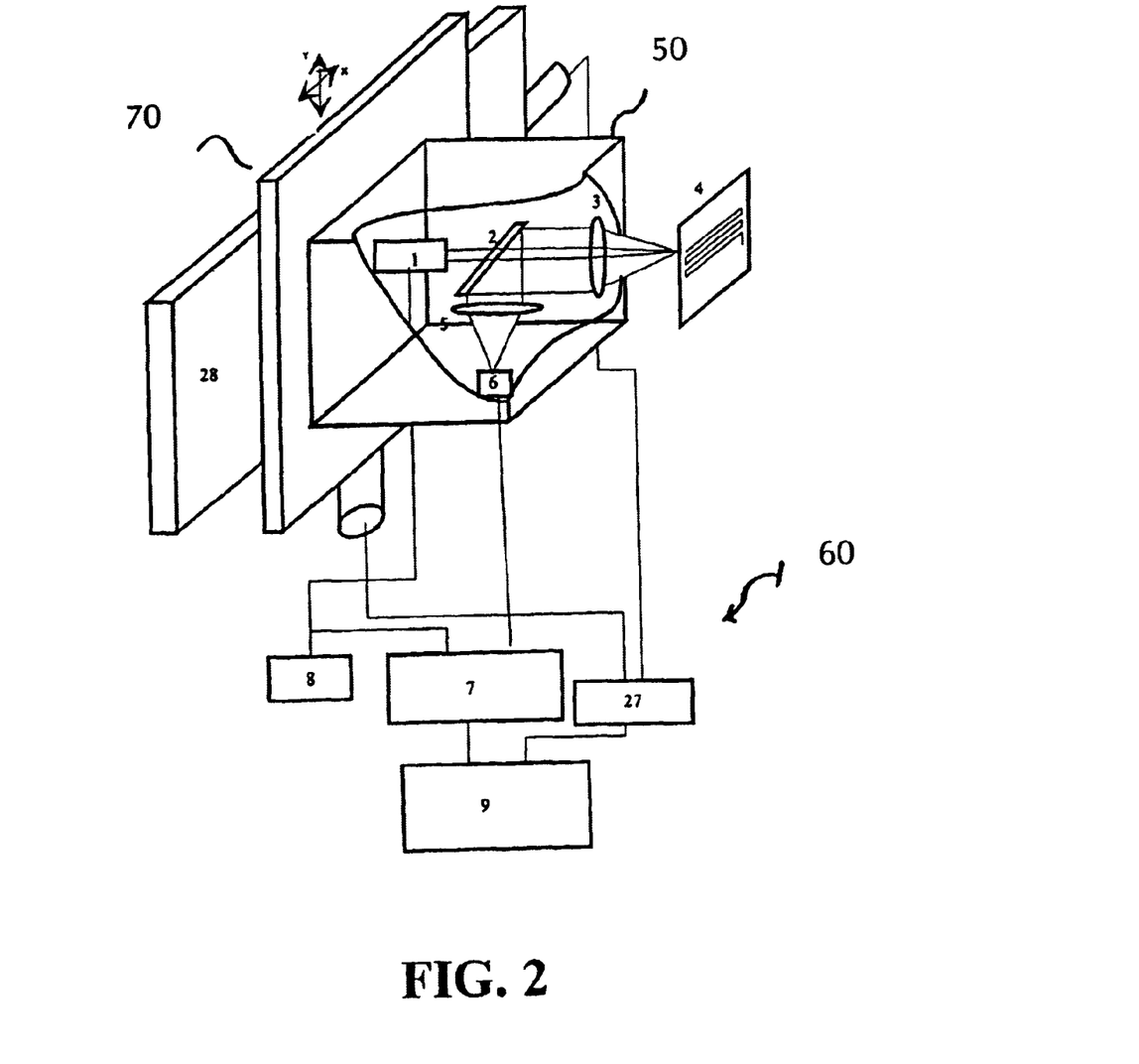
FIG. 2 is a diagram illustrating a detection system according to a first preferred embodiment of the present invention.

FIG. 2 is a diagram illustrating a detection system according to a first preferred embodiment of the present invention. As illustrated in FIG. 2, the system comprises a MIR detection unit 50, a processing unit 60, and a scanning unit 70. The system provides two-dimensional (X and Y planes) scanning of cracks and corrosion located under a paint layer on object 4 and imaging on a display of a computer 9.

The MIR detection unit 50 includes an MIR light source. Although the MIR light source is illustrated in FIG. 2 as IR laser diode 1, other MIR sources such as a light emitting diode (LED) or a heat lamp could also be used.

The laser beam is focused by lens 3 on the paint layer of object 4, which has a material abnormality 55 such as cracks or corrosion beneath it. The laser beam is scanned across the object in X and Y directions and the beam is focused on the area of the coated surface at a certain angle to remove reflected light by the coated surface from the light scattered by the abnormality beneath the illuminated area of the coated surface. These linear scanning movements of the laser beam are generated, for example, by the linear movements of stages 28, which are included in the scanning unit and are preferably operated under a motor control.

A photodetector 6, which is sensitive to the wavelength of the laser diode 1, is provided to receive a portion of the reflection by the object 4, a beam splitter 2, and a focusing lens 5. For example, an InSb Photodetector (PD) is preferable for the wavelength range of 1.8 μm to 5.5 μm, and an HgCdTe PD is preferable for the high frequency modulation. A generator 8 provides a high frequency signal to the bias-tee to perform laser light intensity modulation. The photodetector 6 detects modulated light reflected from the object 4, that is, light scattered from the corrosion or metal under the paint, and creates a high frequency modulated analog electrical signal. A lock-in amplifier 7 (or bandpass-low pass filters) processes signals from the photodetector 6 in a conventional manner to derive optical characteristics from the object 4. An AC modulated current is produced by the RF generator 27, and the modulated analog electrical signal is processed by the lock-in amplifier 7, and digitized and stored in the computer 9 to produce 2-D image.

Figure 11:
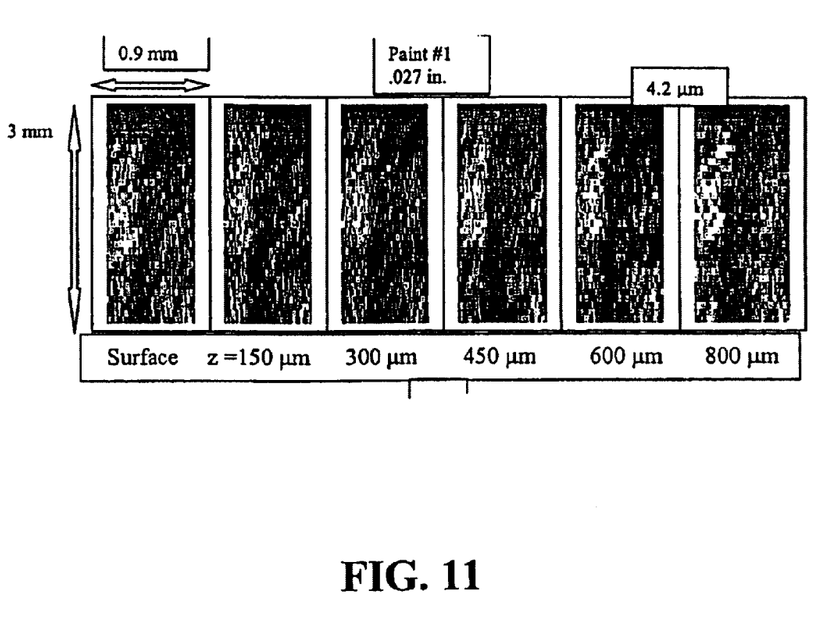
FIG. 11 illustrates a series of –2-D images at different depths of a crack below a paint surface.

FIG. 11 illustrates a series of 2-D images of a crack below a paint surface at different depths (z). The images illustrated in FIG. 11 are an example of the images that are displayed from the computer 9.

Referring to FIG. 11, a series of images (with limited 36×128 scan pixel resolution) at different depths (z) within the crack over coated with paint (0.0027 in. thick) obtained by adjusting the z-position of the laser focal spot are illustrated. The resolution can be improved using modified software, a demodulation system and optical design.

In addition, this series of 2-D images for different z-values can be combined utilizing computer image processing to produce a 3-D sub-surface tomographic image of the micro-rack.

Figure 3:
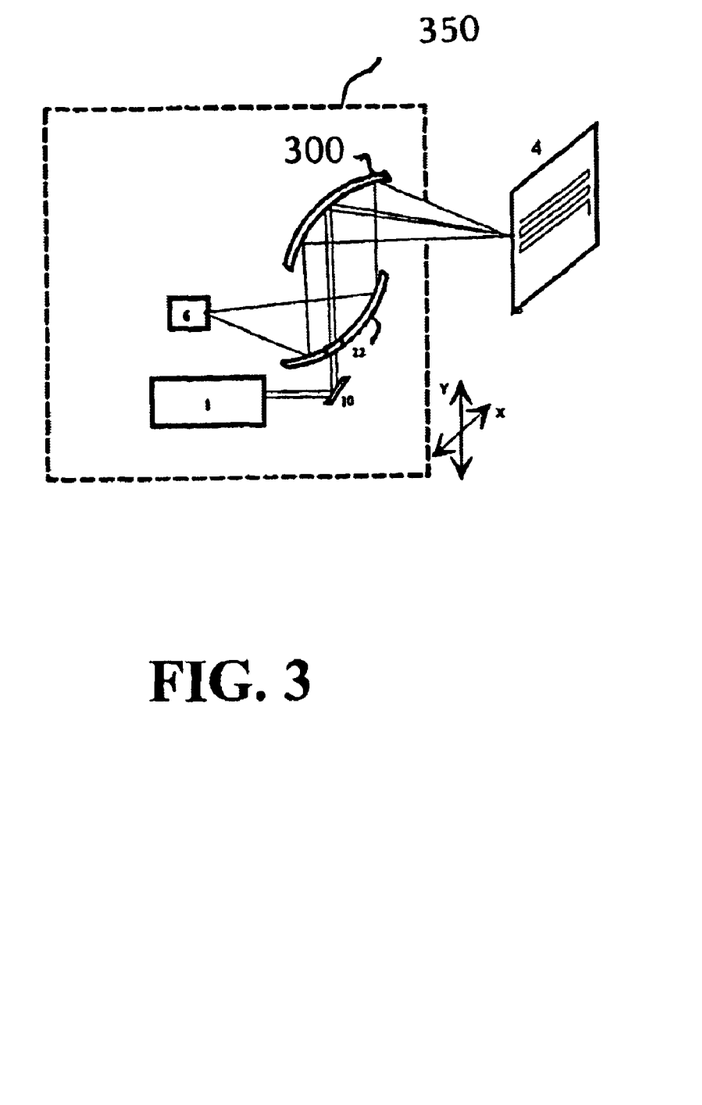
FIG. 3 is a diagram illustrating a detection system according to a second preferred embodiment of the present invention.

FIG. 3 is a diagram illustrating a detection system according to a second preferred embodiment of the present invention. Specifically, FIG. 3 illustrates an alternate embodiment of the MIR detection unit 50 illustrated in FIG. 2. In FIG. 3, the MIR detection unit 350 is comprised of an off-axis parabolic mirror (OPM) 300, an OPM with a hole in the middle 22, and mirror 10 rather than focusing lens 3 and 5 of the MIR detection unit 50 illustrated in FIG. 2.

In FIG. 3, the laser 1 projects a beam that is reflected off mirror 10 and is transmitted through a hole in OPM 22. The transmitted beam is then reflected off of OPM 300 to the target 4. The light reflected off the target 4 is then received by the OPM 300, reflected to OPM 22, and then directed to photodetector 6.

Figure 4:
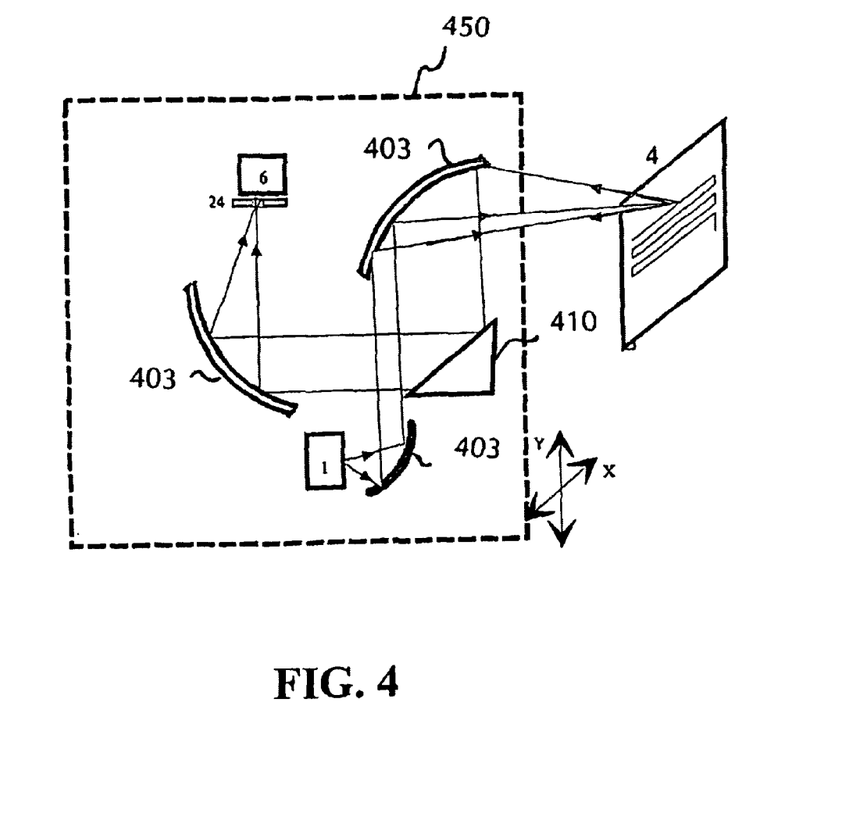
FIG. 4 is a diagram illustrating a detection system according to a third preferred embodiment of the present invention.

FIG. 4 is a diagram illustrating a detection system according to a third preferred embodiment of the present invention. Specifically, FIG. 4 illustrates an alternate embodiment of the MIR detection unit 50 illustrated in FIG. 2. In FIG. 4, the MIR detection unit 450 is comprised of a number of off-axis parabolic mirrors (OPM) 403, and prism 410 rather than focusing lens 3 and 5 of the MIR detection unit 50 illustrated in FIG. 2. In addition, the MIR detection unit 450 includes a pinhole filter 24, which is utilized for providing confocal depth resolution.

In FIG. 4, the laser 1, projects a beam, which is directed by the OPMs 403 to the target 4. The light reflected by the target 4 is then captured and directed to the photodetector 6 by the OPMs 403 and the prism 410. As indicated above, the pinhole filter located directly before the photodetector 4 provides confocal depth resolution.

Figure 5:
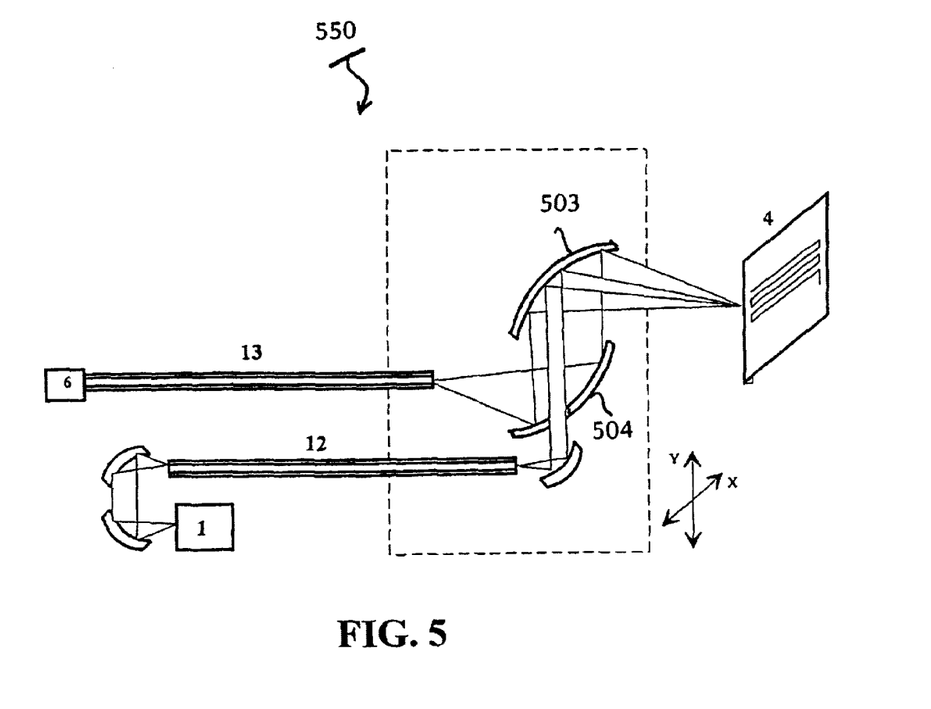
FIG. 5 is a diagram illustrating a detection system utilizing fiber optic cables according to a fourth preferred embodiment of the present invention.

FIG. 5 is a diagram illustrating a detection system utilizing fiber optic cables 12 and 13 according to a fourth preferred embodiment of the present invention. In order to increase the distance from the object/target 4 to the imaging device in the embodiment of FIG. 5 in accordance with the present invention, the OPM 503 is placed at a focal length distance (f), from the object 4 and the end of the single-mode fiber 13 (5–8 $\mu$m diameter) is placed at the front of the OPM 504 with a hole in the middle at the f distance with the f in the range of 25 to 100 mm. The beam diameter at the object 4 is equal to the diameter of the single-mode fiber 12 [in this case]. The MIR detection unit 550 employs a single mode fiber optics cable 12 with a core diameter in the range of 5 to 10 $\mu$m to deliver a light from the laser 1 to the target 4. Output fiber 13 is connected to the photodetector 6. In this case, the input-output fibers 12 and 13 and OPM 503 can be scanned in the x and y directions. A fiber optic based rotator can be used to eliminate intensity losses of the light reflected by the object 4.

Figure 6:
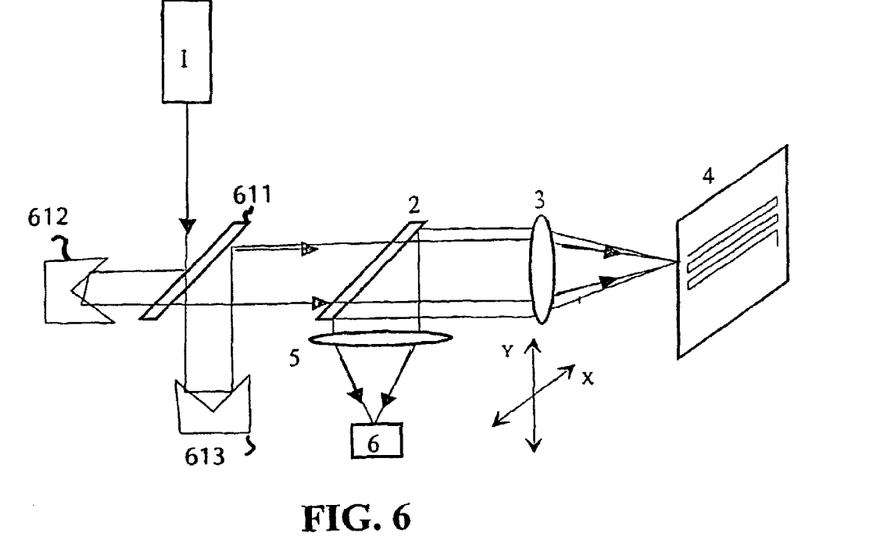
FIG. 6 is a diagram illustrating a detection system utilizing a Michelson interferometer according to a fifth preferred embodiment of the present invention.

FIG. 6 is a diagram illustrating a detection system utilizing a Michelson interferometer according to a fifth preferred embodiment of the present invention. In order to increase the sensitivity of the crack detection, the laser beam is split by a beam splitter 611 into two beams. Optical elements 611, and corner prisms 612 and 613 produce a Michelson interferometer. In this embodiment, after being split by element 611, two coherent laser beams propagate parallel to each other and are focused on the object 4 in the common spot. The optical delay between two beams can be changed by the translation of the corner prism 612 and has to be equal to $\pi/2$ to produce destructive interference in the focal spot. When the scanning surface of target 4 is plane on the order of $\pi/2$ (0.5–1 $\mu$m), the reflected intensity is very small. At the surface scratches the optical delay between two beams can be changed significantly, producing a big reflected intensity from the crack. This signal can be recorded by the detection system producing significant sensitivity to the cracks in the 2-D scanning image.

Figure 7:
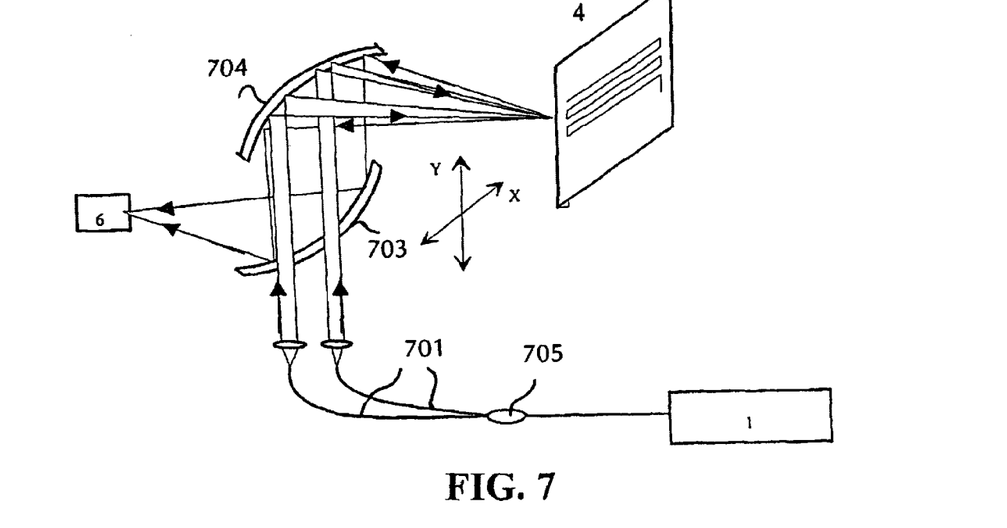
FIG. 7 is a diagram illustrating a detection system utilizing an alternate Michelson interferometer according to a sixth preferred embodiment of the present invention.

FIG. 7 is a diagram illustrating a detection system utilizing an alternate Michelson interferometer according to a sixth preferred embodiment of the present invention. In FIG. 7, fiber optic cables 701 are used to carry two beams, which are produced by the fiber-optic beam splitter 705 from the laser beam 1, to the object 4. These two beams are transmitted through two holes in the OPM 703 and are focused on the object 4 in the common spot by another OPM 704.

Figure 8:
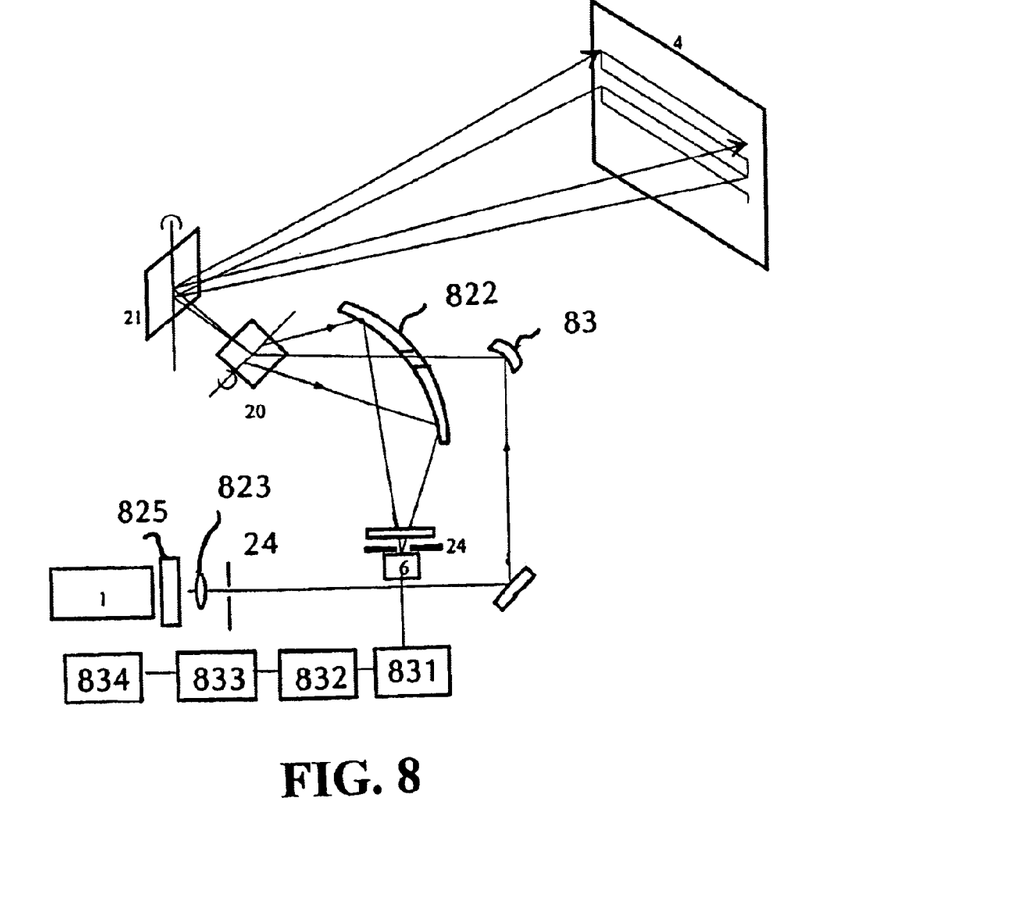
FIG. 8 is a diagram illustrating a detection system utilizing scanning mirrors according to a seventh preferred embodiment of the present invention.

FIG. 8 is a diagram illustrating a detection system utilizing scanning mirrors 20 and 21 according to a seventh preferred embodiment of the present invention. In FIG. 8, the device can be realized as a hand-held laser imager. The laser beam is scanned in X and Y directions by the mirrors 20, 21. The light reflected by the object 4 is collected by the off-axis parabolic mirror (OPM) 822. This mirror has a hole in the middle in the range of 0.3 to 2 mm. In the front of photodetector 6, a notch filter 826 is installed. A pinhole 24 (5–20 $\mu$m diameter) is placed in the focus of lens 823 at a distance, for example, double focus distance (dfd), from the parabolic mirror 83. The target 4 is placed at the dfd from the mirror 83 so that the pinhole 24 is focused on the target 4. An acousto-optical modulator 825 is applied for intensity modulation. An electronic system for signals processing employs high-frequency bandpass filter 831 with the central frequency equal to the frequency driven by the acousto-optical modulator 825. A logarithmic amplifier 832 is used to utilize a high dynamic range and a low pass filter 833 is connected with an analog-digital converter 834. The digital signal is then sent to computer 9 for processing.

Figure 9:
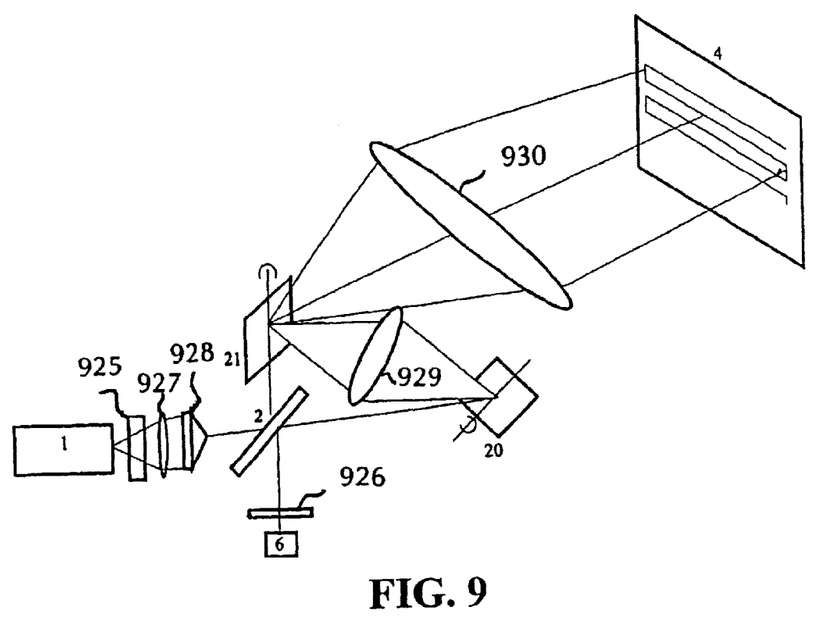
FIG. 9 is a diagram illustrating a detection system utilizing scanning mirrors according to an eighth preferred embodiment of the present invention.

FIG. 9 is a diagram illustrating a detection system utilizing scanning mirrors according to an eighth preferred embodiment of the present invention. In FIG. 9, another realization of the possible hand-held laser imager is illustrated. This system employs a conical lens 928 to produce a beam with diameter in the range of 5 to 20 $\mu$m over a distance of up to 200 mm along the axis of the beam. The conical lens 928 produces a non-diverging axicon beam. The diameter of the beam central peak, $1_0$, is determined by the wavelength $\lambda$ and wavefront cone angle $\alpha$ $$l_0 = 0.26 \lambda / \alpha \tag{1}$$

The beam breaks into a "donut" shaped intensity distribution after distance $Z_0$ where $Z_0$ is given by the expression:

$$Z_0 = R_0 / \alpha \tag{2}$$

where $2R_0$ is a diameter of the beam. The larger $R_0$, the less relative energy goes into central peak $1_0$.

For example, for $R_0 = 10$ mm, $Z_0 = 100$ mm, $\lambda = 1.3$ $\mu$m $$l_0 = 0.76 \lambda Z_0 / R_0 = 0.76 \times 1.3 \ 10^{-3} \times 10^2 / 10 = 10 (\mu m) \tag{3}$$

In order to increase the diameter of the beam a lens 927 is applied. A telescope system 929 focuses an axis of mirror 20 to the mirror 21 plane. An axis of mirror 21 is placed at the focal plane of the lens 930, which transmits and receives the light to and from object 4.

As described above, the present invention provides systems and methods for non-destructively detecting material abnormalities beneath a coated surface, in which a mid-infrared (MIR) detection unit illuminates an area of the coated surface and detects light reflected from the illuminated area of the coated surface, a processing unit produces an image from optical characteristics received from the MIR detection unit, and a scanning unit moves the MIR detection unit to a next area.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A system for non-destructively detecting material abnormalities beneath a coated surface, comprising:

a mid-infrared (MIR) detection unit for illuminating an area of the coated surface and detecting light reflected from the illuminated area of the coated surface; and a processing unit for producing an image from optical characteristics received from the MIR detection unit.

2. The system as recited in claim 1, further comprising a scanning unit for moving the MIR detection unit to a next area of the coated surface.

3. The system as recited in claim 2, wherein the scanning unit comprises at least one stage for moving the system in at least one of X and Y directions.

4. The system as recited in claim 2, wherein the scanning unit comprises a plurality of mirrors for scanning light emitted from the MIR detection unit in at least one of X and Y directions.

5. The system as recited in claim 1, wherein the processing unit comprises:

a radio frequency generator for generating a high frequency signal to perform light intensity modulation;

a lock-in amplifier for processing signals received from the MIR detection unit; and a computer for digitizing and storing the processed signals to produce a 2-D image.

6. The system as recited in claim 5, wherein the computer creates 3-D images by computer processing multiple 2-D images of an area, which are determined at different depths (Z) below the coated surface.

7. The system as recited in claim 1, wherein the MIR detecting unit comprises:

a mid-infrared (MIR) light source for providing MIR light for illuminating the area of the coated surface; and a photodetector for detecting light scattered by an abnormality beneath the illuminated area of the coated surface.

8. The system as recited in claim 7, further comprising at least one fiber optic cable for transmitting at least one of the MIR light from the MIR light source and the scattered light to the photodetector.

9. The system as recited in claim 7, further comprising at least one pinhole filter for providing confocal depth resolution.

10. The system as recited in claim 7, wherein the MIR light source is at least one of a light emitting diode (LED) and a laser.

11. The system as recited in claim 7, wherein the MIR light is focused on the area of the coated surface at a certain angle to remove reflected light by the coated surface from the light scattered by the abnormality beneath the illuminated area of the coated surface.

12. The system as recited in claim 7, wherein the MIR light source has wavelength range from 2 $\mu$m to 5.5 $\mu$m.

13. The system as recited in claim 1, wherein the surface is metal.

14. The system as recited in claim 1, wherein the coating is paint.

15. The system as recited in claim 1, wherein the abnormalities include at least one of deterioration, corrosion, and cracking.

16. A method for non-destructively detecting material abnormalities beneath a coated surface, comprising the steps of:

illuminating an area of the coated surface by a mid-infrared (MIR) light source;

detecting light reflected from the illuminated area of the coated surface utilizing a photodetector;

measuring optical characteristics of the reflected light; and producing a 2-D image from information received from the photodetector.

17. The method as recited in claim 16, further comprising scanning a next area of the coated surface.

18. The method as recited in claim 17, wherein the step of scanning the next area comprises moving the MIR light source in at least one of X and Y directions.

19. The method as recited in claim 17, wherein the step of scanning the next area comprises rotating a plurality of mirrors for scanning light emitted from the MIR light source in at least one of X and Y directions.

20. The method as recited in claim 16, wherein the step of producing the 2-D image is performed utilizing a computer.

21. The method as recited in claim 16, further comprising creating a 3-D image of an area by computer processing multiple 2-D images of the area, which are determined at different depths below the coated surface.

22. The method as recited in claim 16, wherein the MIR light source is at least one of a light emitting diode (LED) and a laser.

23. The method as recited in claim 16, wherein the MIR light source is focused on the area of the coated surface at a certain angle to remove reflected light by the coated surface from light scattered by the abnormality beneath the illuminated area of the coated surface.

24. The method as recited in claim 16, wherein the MIR light source has wavelength range from 2 $\mu$m to 5.5 $\mu$m.

25. The method as recited in claim 16, wherein the surface is metal.

26. The method as recited in claim 16, wherein the coating is paint.

27. The method as recited in claim 16, wherein the abnormalities include at least one of deterioration, corrosion, and cracking.

* * * * *